US009075016B2

(12) United States Patent
Groves

(10) Patent No.: US 9,075,016 B2
(45) Date of Patent: Jul. 7, 2015

(54) AUTOMATED CONTROL OF ANALYTICAL SAMPLING WITH ENVIRONMENTAL MONITORING SYSTEM

(75) Inventor: Bruce D. Groves, Madison, NJ (US)

(73) Assignee: EMILCOTT ASSOCIATES, INC., Morristown, NJ (US)

( * ) Notice: Subject to any disclaimer, the term of this patent is extended or adjusted under 35 U.S.C. 154(b) by 190 days.

(21) Appl. No.: 13/456,786

(22) Filed: Apr. 26, 2012

(65) Prior Publication Data

US 2012/0215445 A1     Aug. 23, 2012

Related U.S. Application Data

(63) Continuation-in-part of application No. 12/650,951, filed on Dec. 31, 2009, now Pat. No. 8,584,509.

(60) Provisional application No. 61/479,171, filed on Apr. 26, 2011, provisional application No. 61/479,170, filed on Apr. 26, 2011.

(51) Int. Cl.
| | |
|---|---|
| *G06F 19/00* | (2011.01) |
| *G01N 1/14* | (2006.01) |
| *G01N 27/66* | (2006.01) |
| *G01N 1/22* | (2006.01) |
| *G01N 1/26* | (2006.01) |
| *G01N 27/62* | (2006.01) |

(52) U.S. Cl.
CPC .............. *G01N 27/66* (2013.01); *G01N 1/2294* (2013.01); *G01N 1/26* (2013.01); *G01N 27/62* (2013.01)

(58) Field of Classification Search
CPC ..... G01N 1/26; G01N 1/2294; G01N 1/2273; G01N 27/66; G01N 27/62; G01N 27/70; G01N 7/10; G01N 2030/642

USPC ................................... 324/466, 459, 464
See application file for complete search history.

(56) References Cited

U.S. PATENT DOCUMENTS

| | | | | |
|---|---|---|---|---|
| 4,080,832 | A * | 3/1978 | Moody et al. ............... | 73/863.23 |
| 4,855,909 | A * | 8/1989 | Vincent et al. ............ | 346/33 ME |
| 5,333,785 | A * | 8/1994 | Dodds et al. ..................... | 239/69 |
| 5,654,498 | A | 8/1997 | Kessel | |
| 5,832,411 | A * | 11/1998 | Schatzmann et al. ........... | 702/23 |
| 5,878,813 | A * | 3/1999 | Ridgeway, Jr. ................ | 166/162 |
| 6,123,820 | A * | 9/2000 | Bergkuist et al. ............. | 204/411 |
| 6,321,588 | B1 * | 11/2001 | Bowers et al. ............... | 73/24.01 |
| 6,333,632 | B1 | 12/2001 | Yang et al. | |
| 6,459,079 | B1 * | 10/2002 | Machlinski et al. .......... | 250/286 |
| 6,931,913 | B2 * | 8/2005 | Manoosingh ................ | 73/31.01 |
| 6,945,127 | B2 * | 9/2005 | Van Netten ................ | 73/863.23 |
| 7,241,989 | B2 | 7/2007 | Miller | |
| 7,302,313 | B2 | 11/2007 | Sharp et al. | |
| 7,704,748 | B2 | 4/2010 | Scaheffer et al. | |
| 7,777,179 | B2 | 8/2010 | Chen et al. | |
| 7,788,970 | B2 * | 9/2010 | Hitt et al. .......................... | 73/73 |
| 8,054,082 | B2 | 11/2011 | Brothier et al. | |
| 8,205,483 | B1 | 6/2012 | Peterson et al. | |

(Continued)

*Primary Examiner* — Jermele M Hollington
*Assistant Examiner* — Christopher McAndrew
(74) *Attorney, Agent, or Firm* — Graham Curtin, P.A.

(57) ABSTRACT

A new and improved environmental field monitor station is disclosed. A novel and analytical sampling control device with a removable analytical sample collection device is described. Also a novel field station having the analytical sampling control device with the removable analytical sample collection device is described. Methods of using and controlling the analytical sampling control device, both within in a field station and from a base station, are described.

17 Claims, 5 Drawing Sheets

(56) References Cited

U.S. PATENT DOCUMENTS

| | | |
|---|---|---|
| 8,258,794 B2 | 9/2012 | Rziha |
| 8,336,402 B2 | 12/2012 | Glezer |
| 8,479,558 B2 | 7/2013 | Dimmler et al. |
| 2002/0048818 A1 | 4/2002 | Sakairi et al. |
| 2006/0173579 A1* | 8/2006 | Desrochers et al. .......... 700/276 |
| 2007/0012185 A1 | 1/2007 | Taylor et al. |
| 2008/0148816 A1 | 6/2008 | Groves |
| 2009/0090167 A1 | 4/2009 | Groves |
| 2009/0095054 A1 | 4/2009 | Groves |
| 2009/0113990 A1 | 5/2009 | Groves |
| 2010/0201542 A1* | 8/2010 | Harnett .................. 340/870.28 |

\* cited by examiner

AUTOMATED CONTROL OF ANALYTICAL SAMPLING WITH ENVIRONMENTAL MONITORING SYSTEM

CROSS REFERENCE TO RELATED APPLICATIONS

The present application claims the benefit of U.S. Provisional Patent Application Ser. No. 61/479,171 filed on Apr. 26, 2011 and of U.S. Provisional Patent Application Ser. No. 61/479,170 filed on Apr. 26, 2011, both of which are incorporated by reference herein in their entireties.

The present application is also a continuation-in-part of U.S. patent application Ser. No. 12/650,951, filed Dec. 31, 2009, which is incorporated by reference herein in its entirety.

BACKGROUND

It is important to monitor environmental conditions in many situations. Those situations include construction and environmental clean-up. For example, environmental monitoring can ensure that a construction project or an environmental clean-up project is creating an environmental problem by disturbing and then spreading an environmental contamination at a site. When the monitoring equipment detects a problem, it can notify an environmental monitoring team and steps can be taken to rectify the situation.

It is important to have an accurate understanding of what is happening in environmentally sensitive areas. However, today's environmental measuring systems and method do not provide all of the information needed.

Accordingly, new and improved environmental sampling components and systems are needed. Further, new and improved methods of environmental sampling are required.

SUMMARY

In accordance with one aspect of the present invention, an environmental field station system comprises an enclosure with an air intake and one or more environmental sensors mounted in the enclosure, each of the environmental sensors detecting an environmental condition. It further comprises an analytical sampling collection device mounted in the enclosure, each of the analytical sampling collection devices having a controllable inlet block valve, a flow meter with an output, a removable analytical sample capture device and a controllable air pump and a processor mounted in the enclosure, the processor being connected to the one or more environmental sensors to receive environmental conditions sensed by the one or more environmental sensors; the processor also being connected to the controllable inlet block valve and the controllable air pump in the analytical sample capture device. The processor opens the controllable inlet block valve and/or turns on the controllable air pump in the sample collection device when one of the one or more environmental sensors detects an environmental condition warranting initiation of sample collection.

In accordance with a further aspect, the one or more environmental sensors are selected from the group consisting of: dust sensors, gas sensors, vapor sensors, noise sensors, vibration sensors, radiation sensors and weather instruments.

In accordance with another aspect, the analytical sample capture device is a tube containing a sampling medium or sorbent selected from the group consisting of: charcoal, Tenax, and silica gel.

In accordance with another aspect, the analytical sample capture device is a cartridge with a filter or other sampling medium selected from the group consisting of PVC, MCEF, and PUF.

In accordance with another aspect, the analytical sample capture device is an evacuated canister.

In accordance with another aspect, the analytical sample capture device is a sample collection bag.

In accordance with another aspect, the sample collection bag is Tedlar or Mylar.

In accordance with another aspect, the processor is connected to the flow meter in the sample collection device and a flow rate is reported from the flow meter to the processor.

In accordance with another aspect, the processor is preprogrammed to determine when the environmental condition warrants initiation of sample collection.

In accordance with another aspect, the processor determines that the environmental condition warrants initiation of sample collection when the environmental condition exceeds a predetermined threshold.

In accordance with a further aspect of the present invention, an environmental monitoring system is provided. It includes a base station; a plurality of environmental field stations, each comprising an enclosure with an air intake; one or more environmental sensors mounted in the enclosure, each of the environmental sensors detecting environmental conditions; a analytical sampling control device mounted in the enclosure, each of the analytical sampling control devices having a controllable inlet block valve, a flow meter with an output, a removable analytical sample capture device and a controllable air pump; and a processor mounted in the enclosure, the processor being connected to the one or more environmental sensors to receive environmental conditions sensed by the one or more environmental sensors; the processor also being connected to the controllable inlet block valve and the controllable air pump in the analytical sampling control device; wherein the processor opens the controllable inlet block valve and/or turns on the controllable air pump in the analytical sampling control device when one of the one or more environmental sensors detects environmental conditions, as previously specified by the operator or programmed or calculated in the processor, warranting initiation of sample collection; and the processor in each of the environmental field stations communicates with the base station and the base station controls a analytical sampling control device in one of the plurality of environmental field stations based on a detected environmental condition in another of the plurality of environmental field stations.

In accordance with another aspect, the analytical sample capture device in the environmental monitoring system is a tube containing a sampling medium or sorbent selected from the group consisting of: charcoal, Tenax, and silica gel.

In accordance with another aspect, the analytical sample capture device in the environmental monitoring system is a cartridge with a filter or other sampling medium, selected from the group consisting of PVC, MCEF, and PUF.

In accordance with another aspect, the analytical sample capture device in the environmental monitoring system is an evacuated canister.

In accordance with another aspect, the analytical sample capture device in the environmental monitoring system is a sample collection bag comprising Tedlar or Mylar.

In accordance with a further aspect of the present invention, a analytical sampling control device is provided. It has an enclosure with an air intake port, a first electrical input port, a second electrical input port and an electrical output port, a controllable inlet block valve mounted inside the enclosure and having an input, an output and an electrical control input, the input connected to the air intake port in the enclosure and the electrical control input being connected to the first electrical input port in the enclosure wherein the inlet block valve is opened or closed according to a state of the electrical control input, a flow meter mounted inside the enclosure having an input, an output and an electrical output, the input of the flow meter being connected to the output of the controllable inlet block valve and the electrical output being connected to the electrical output port in the enclosure, the electrical output of the flow meter providing a rate of air flow during operation of the flow meter and a removable analytical sample capture device mounted inside the enclosure having an input and an output, the input of the analytical sample capture device being connected to the output of the flow meter, the analytical sample capture device having a removable sample capture section. It further includes a controllable air pump mounted inside the enclosure having an input and an electrical control input, the input of the air pump being connected to the output of the analytical sample capture device and the electrical control input of the air pump being connected to the second electrical input port of the enclosure.

The enclosure can further include an air exhaust and an output of the controllable air pump is connected to the air exhaust.

The removable sample capture section can be selected from the group consisting of: a tube, a cartridge, an evacuated canister, a PUF sampler and a sample collection bag.

Methods of using these devices are also provided.

DESCRIPTION

In accordance with an aspect of the present invention, today's automated real-time environmental monitoring system are enhanced to include the capability to initiate and control the capture of air samples for purposes of subsequent laboratory analysis from a vicinity of the site or building where the real-time system is operational. Examples of known environmental monitoring systems are described in U.S. patent application Ser. Nos. 12/333,856; 12/333,958; 12/334,061; 12/650,951 and 12/683,702, which are hereby incorporated by reference into this document.

Today, once analytical samples are captured, they are analyzed in an offsite or onsite (field) laboratory, on a batch basis, to determine whether a substance of interest is present and in what concentration.

Figure 1:
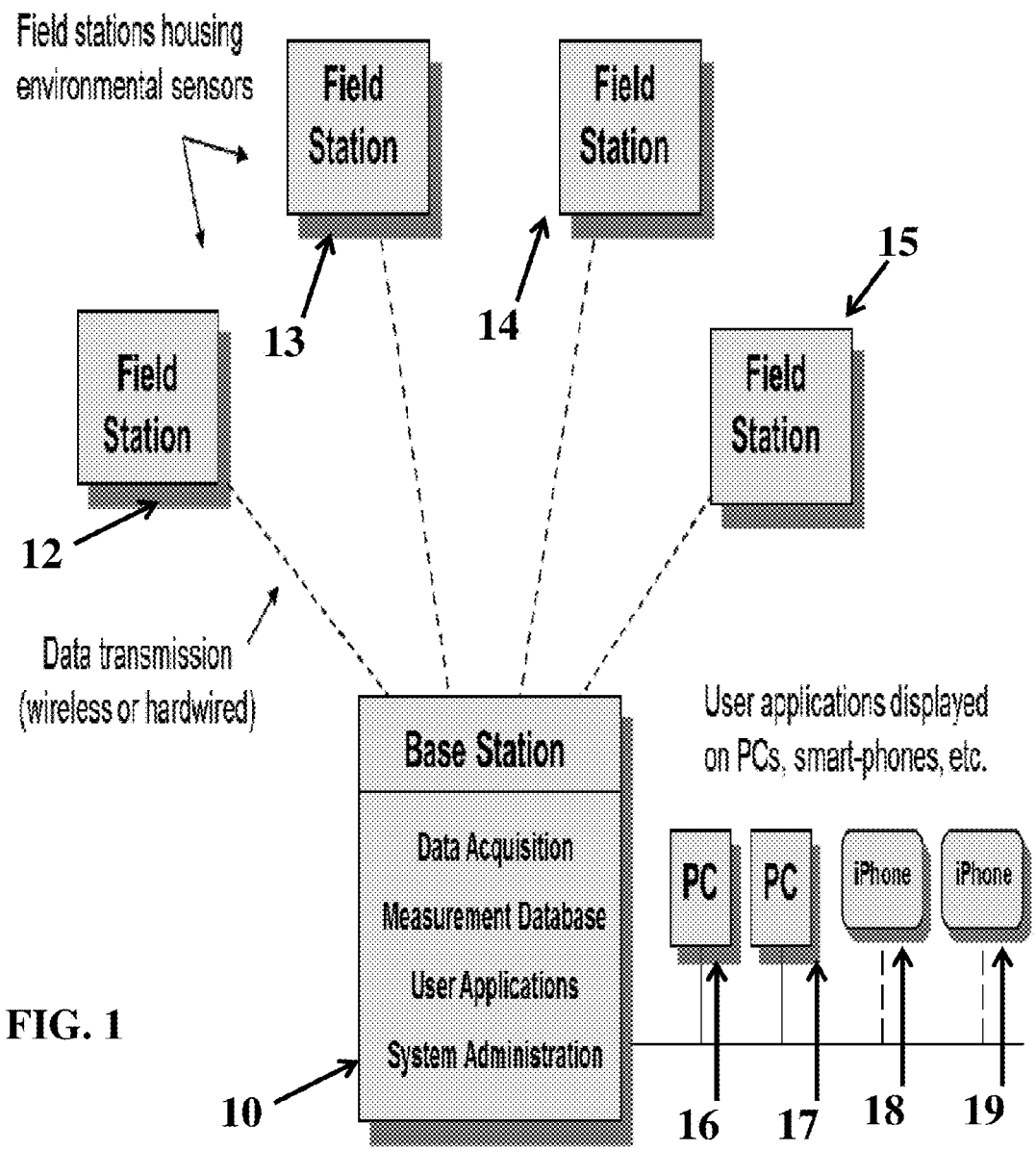
FIG. 1 illustrates a configuration of a real-time environmental monitoring system.
Figure 2:
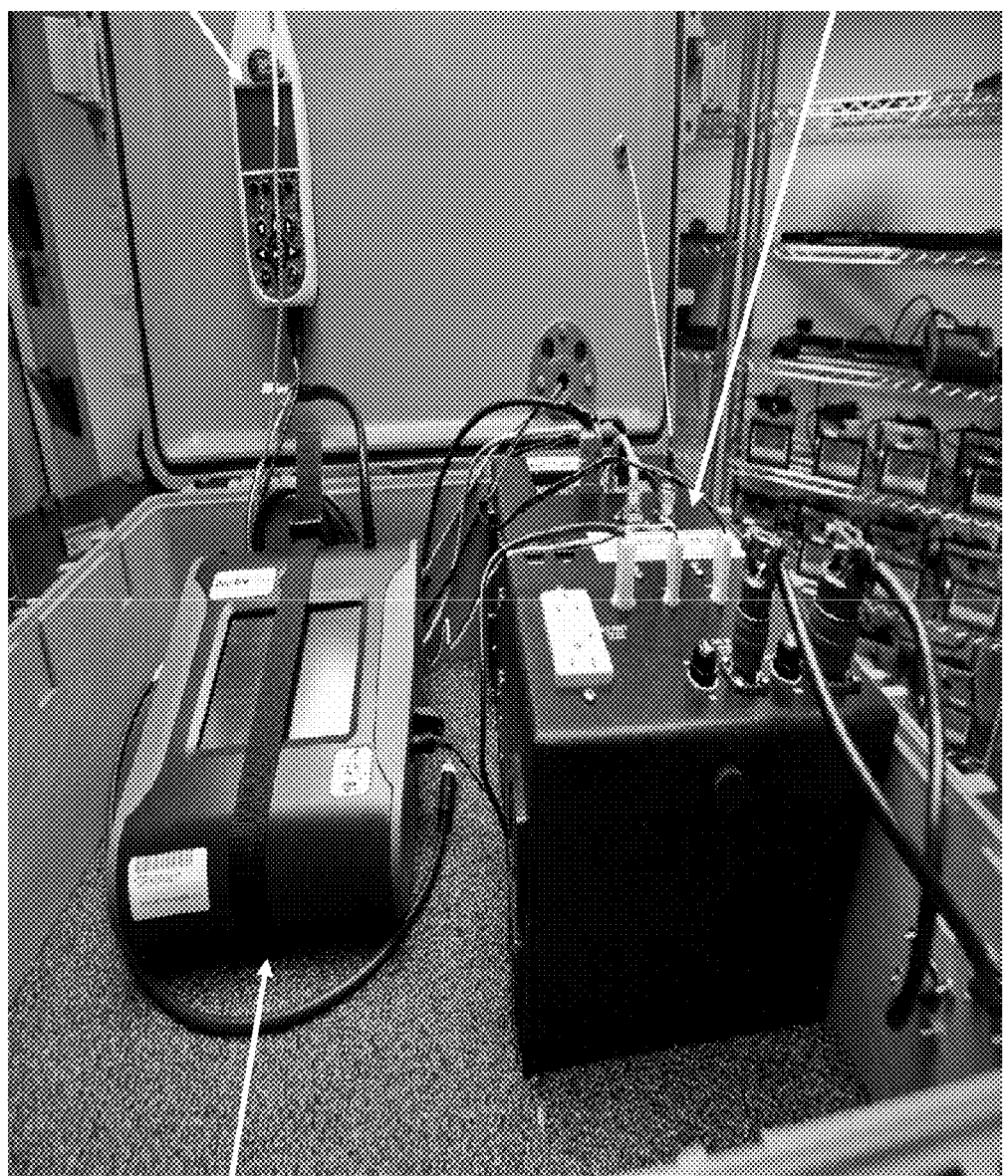
FIG. 2 illustrates an example of the internal components of a field station of a real-time environmental monitoring system in accordance with an aspect of the present invention.
Figure 3:
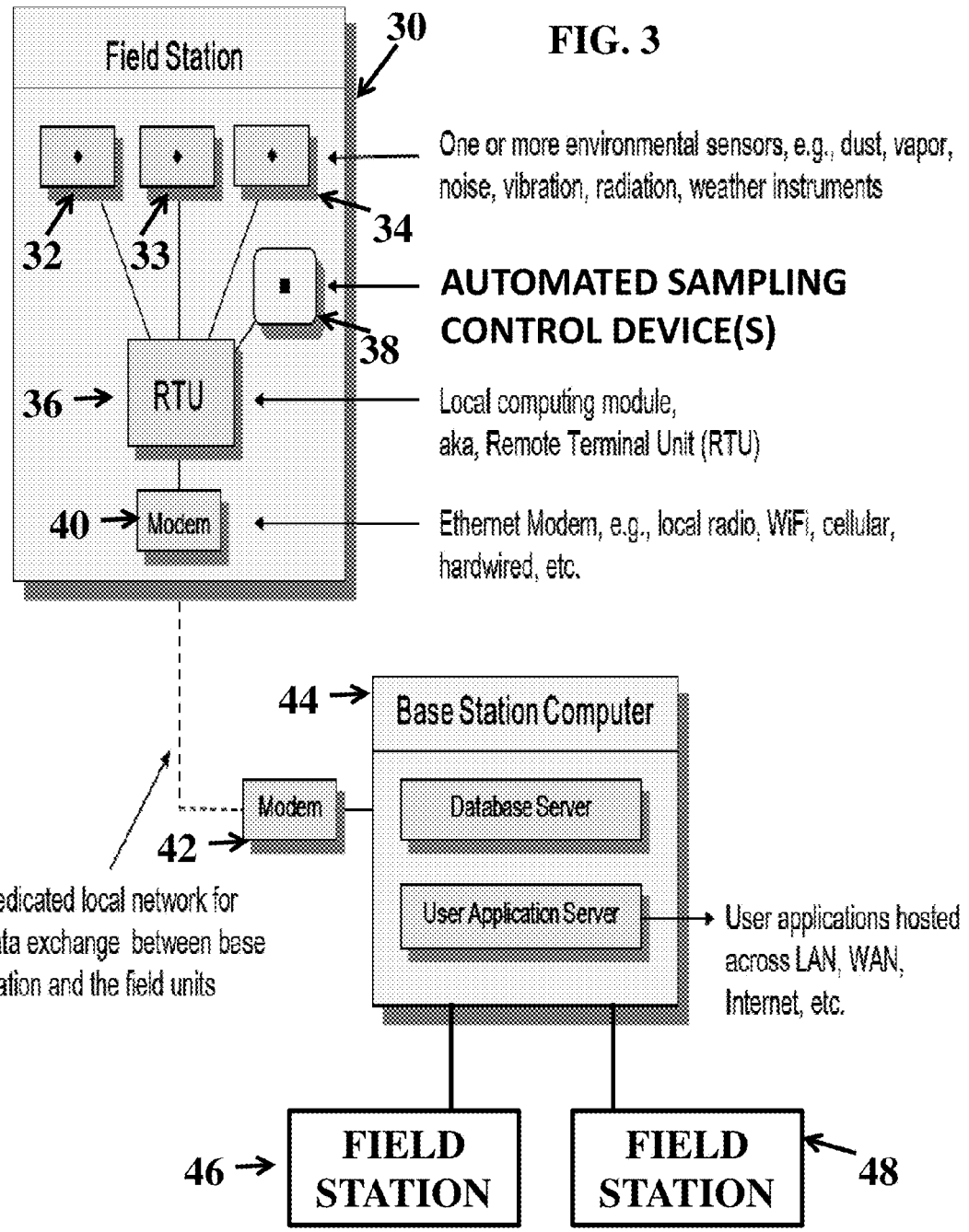
FIG. 3 illustrates a local computing module (RTU) interfaces in accordance with an aspect of the present invention.

The real-time environmental monitoring system includes a base-station computer server and one or more field monitoring stations. The field stations are each equipped with a local computing module of some sort, e.g., remote terminal unit (RTU), smart data-logger, embedded computer, SCADA control module, etc. The base-station may include end-user environmental monitoring applications; a system-wide database of environmental measurements; software application that present graphical displays, produce reports, and generate alarm notifications; and a communication network with the field stations, via wireless telemetry and/or hardwired connections. A schematic representation of such a system is shown in FIG. 1. A photograph of the internal layout of a typical field station is shown in FIG. 2. A schematic representation of the data communication interfaces between the local computing module and other devices is shown in FIG. 3. Note that FIG. 3 also depicts the relationship of an automated sampling device to the local computing module, which is an important aspect of this invention.

The base-station computer and the field computing modules are capable of responding to environmental measurements and subsequently taking actions based on those measurements. For purposes of this invention, these computers are can be connected to automated devices capable of initiating and controlling the capture of an analytical sample. Such configuration would enable the following types of control and monitoring actions:

Opening and closing valves connected to sampling ports for air or liquids.

Starting and stopping sampling pumps or fans, either through software commands to the sampling device, and/or simply turning on and off the power to such devices.

Measuring, in real-time, parameters such as flow rate, pressure, temperature, and duration that can be used to calculate when the capture of a given analytical sample is complete.

In accordance with an aspect of the present invention, the capture of an analytical sample could be initiated by one of the following means:

When a measured environmental parameter within the system reaches a preset threshold level or range, for example an instantaneous value or a calculated time-weighted average of a threshold; or for example when the wind direction reaches a target range.

When a user issues an instruction through a software program running on the base-station and/or the local computing modules in the field stations.

A predetermined time sequence, specified in advance by a user at the base-station and/or the local computing modules in the field stations.

Any combination of the above can be used to control the capture of an analytical sample.

To implement system software to adjust the duration and/or flow rate of a sample based on monitoring of real-time conditions.

The types of analytical sampling media that could be captured by this approach would include one or more of the following options, but not be limited to:

Sampling cartridges, tubes pre-configured with sampling media, and filters used in conjunction with sampling pumps that can be controlled by the system.

Sampling containers operating under negative pressure and having regulator valves governing the rate of inlet flow, e.g., Summa canisters.

High volume fan-driven devices, e.g., PUF samplers.

Flexible bags with airtight inlet valve, for collection and transport of temporary samples, e.g. Tedlar bags filled by sampling pump that can be controlled by the system.

Figure 4:
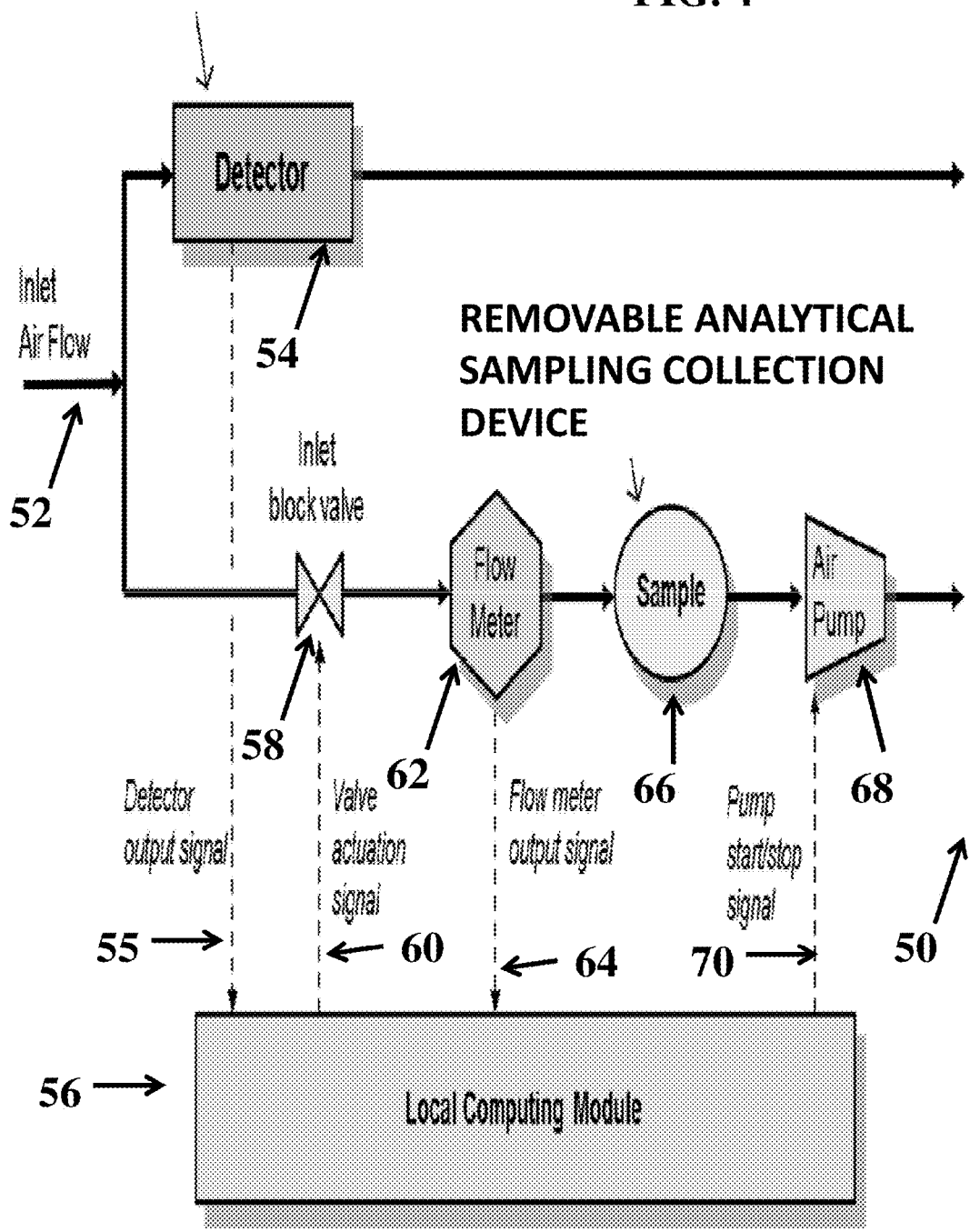
FIG. 4 illustrates the automated capture of analytical samples in accordance with an aspect of the present invention.

An example of the measurement and sampling processes for this automated technique for capturing analytical samples is shown schematically in FIG. 4. The decision logic utilized in this technique is shown schematically in FIG. 5.

There are thousands of specific analytical sampling methods available for environmental, health and safety monitoring. These methods have been established and are stewarded by such organizations as the U.S. Occupational Safety and Health Administration (OSHA), the U.S. Environmental Protection Agency (EPA), and the National Institute for Occupational Safety and Health (NIOSH). Variations on these methods also exist as formally identified "Modified Methods". In addition, there are other viable methods that have been developed by environmental and industrial hygiene laboratories, and manufactures and distributors of chemical products.

Benefits of this invention include:

Rapid response to environmentally-triggered events, initiating the sample collection immediately when triggered rather than waiting for field personnel to traverse the site, investigate with hand-held monitors, etc.

The option to collect samples with inexpensive media (e.g., charcoal filters), and decide after an incident whether it is necessary or beneficial to actually perform laboratory analysis the sample.

Providing an accurate record of the real-time environmental and weather conditions during the intervals when the analytical samples were collected.

Reduction of the dependence on complex and expensive real-time field-mounted instruments, e.g., gas chromatographs, by collecting and transporting samples in flexible bags to an onsite or offsite laboratory.

The relationship between real-time monitoring techniques and the batch nature of laboratory analysis of analytical samples is important to understanding the importance and benefits of this invention. For the vast majority of individual substances of potential environmental interest, no practical or cost-effective real-time measurement technique exists. Laboratory analysis is required to ascertain the presence and concentration of these substances, and such analysis often takes hours, days or weeks to complete. Thus, many real-time measurement techniques provide a surrogate for the actual substances of interest in a given project or application. For example, one well established real-time measurement technique is that of total particulate matter less than 10 microns in diameter (PM–10). However, a project application might be concerned with the possible presence of such specific airborne substances as asbestos, lead, hexavalent chromium, diesel exhaust, soot, etc. In such an application, the real-time system can generate a notification when the level of total particulates reaches an established threshold. This invention enables the immediate initiation of collection of analytical samples upon reaching such a threshold. An ongoing regimen of real-time monitoring supplemented by analytical samples can build a model correlating the two measurement techniques.

Another well-known example of surrogate real-time measurement is monitoring for concentration of total volatile organic and inorganic compounds (TVOC) utilizing a photo-ionization detector (PID) or flame ionization detector (FID). The real-time TVOC measurement reflects the aggregate concentration of a suite of organic compounds, but cannot distinguish among the individual constituents.

Another well-known example of surrogate real-time measurement is for concentration of mercury. Real-time instruments for measuring vapor in air are established and commercially available, e.g., mercury vapor analyzers manufactured by Arizona Instruments, Ion Science, Ohio Lumex, et al. Upon detection of real-time concentrations of mercury vapor, confirmatory analytical laboratory samples can be taken to validate these readings, and/or identify the presence of specific mercury compounds that might be present.

The system is further explained with reference to the drawings. FIG. 1 illustrates a base station 10 in communication with a plurality of field stations 12 to 15. The data transmissions can be wireless or hardwired. The base station 10 is in communication with one or more personal computers 16 and 17 and with other devices, such as iPhones 18 and 19.

FIG. 2 illustrates the internal components of a typical field station 20. The field station can include a noise monitor 24, a particulate monitor 22 and a RTU 26 which is a processor that communicates with the devices in the field station 20 and can provide control of those devices. The RTU 26 also provides communications with a base station, such as the base station 10 shown in FIG. 1.

FIG. 3 shows an exemplary local computing module in an environmental monitoring system in accordance with an aspect of the present invention. A field station 30 includes one or more environmental sensors 32, 33 and 34. These sensors can monitor for a variety of different types of situations. For example, they can be dust sensors, vapor sensors, gas sensors, noise sensors, vibration sensors, and/or weather sensors. The environmental sensors 32, 33 and 34 are connected to a RTU or a local computing module 36. This module 36 includes a processor and a associated computing peripherals that process the sensed data from the environmental sensors 32, 33 and 34. The module 36 also is programmed to provide communications with the environmental sensors 32, 33, and 34 and with other devices, such as a base station 44.

In accordance with another aspect of the present invention, the field station 30 also includes an analytical sampling control device 38. The device is selectively turned on at an appropriate time by the RTU 36 to collect a sample of the air surrounding the field station 30. The analytical sampling control device 38 also communicates with the RTU 36. The RTU 36 provides control signals to the analytical sampling control device 38 and also receives information from the automated collection device 38.

The field station 30 can communicate with the base station 44 through modems 40 and 42. The base station 44 also communicates with other field stations 46 and 48 that are located in diverse locations.

In accordance with one aspect of the present invention, the field station 30 includes an enclosure. The environmental sensors 32 to 34, the analytical sampling control device 38 and the RTU 36 are mounted inside the field station enclosure.

Each field station can vary depending on the specific duty; it can be a rigid box intended for fixed or long-term installation, or a lightweight mobile case capable of being easily moved, or a small container that can be worn by a person to measure an individual's exposure to specified environmental parameters.

FIG. 4 further illustrates a field station 30 in accordance with an aspect of the present invention. The field station device 30 includes an enclosure 50 with an air inlet port 52. Air coming through the air inlet port 52 enters a detector 54. The detector 54 can detect any number of parameters, as described above. An output of the detector 54 is provided to the RTU processor 56. This output provides a sample of the parameter measured by the detector 54. The RTU processor can be programmed for out of normal sample measurements or for measurements that cause some level of concern.

In FIG. 4, an analytical sampling control device includes an air inlet valve 58, a flow meter 62, an analytical sampling collection device 66 and an air pump 68. The air inlet valve 58 includes an electrical input port 60 and an input and an output. The RTU processor 56 provides a signal to the electrical input port 60 to control the opening and closing of the air inlet valve 58. The input of the air inlet valve 58 is connected to an input of the flow meter 62. The flow meter 62 includes an electrical output port 64. The electrical output port 64 is provided to the RTU processor 56. The flow meter 62 provides a measure of the air flow rate through the flow meter during operation on the output port 64. An output of the flow meter 62 is provided to a input of a sample collection device 66. An output of the sample collection device 66 is provided to an input of an air pump 68. The air pump 68 includes an electrical input port 70. The signal provided on the electrical input port 70 controls the operation of the air pump 68. For example, the signal can turn on and off the air pump 68, and optionally control the speed of the air pump 68. In accordance with an aspect of the present invention, the signal on the electrical input port 70 of the air pump 68 is provided by the RTU processor 56. In accordance with another aspect of the present invention, the flow meter 62 can alternatively be located between the sample collection device 66 and the air pump 68.

Figure 5:
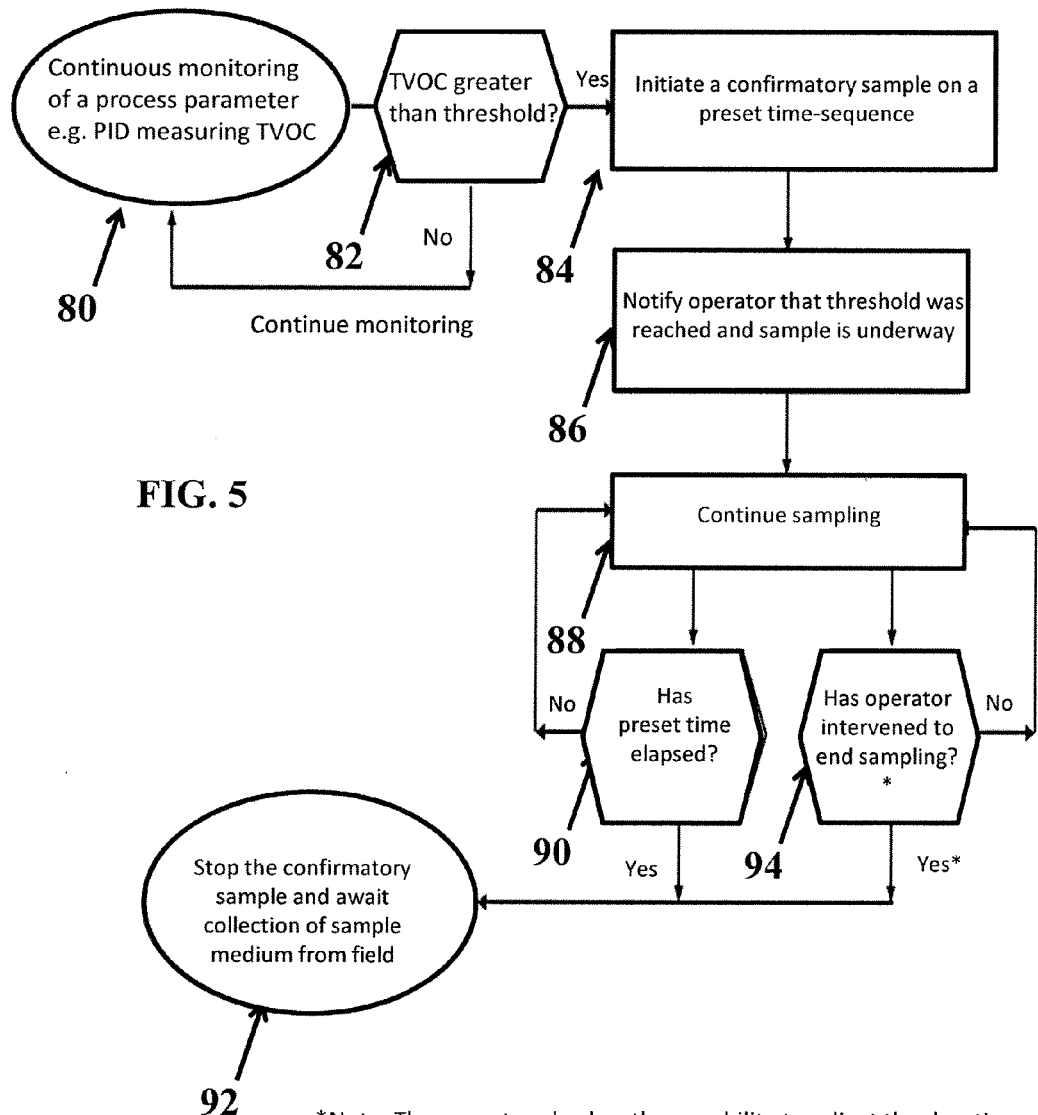
FIG. 5 illustrates decision logic for automated capture of analytical samples in accordance with an aspect of the present invention.

FIG. 5 illustrates a method of operation of the field station of FIG. 4 in accordance with an aspect of the present invention. In step 80, the environmental sensors (or detectors) 54 continuously monitor a process parameter or an environmental condition. That information is sent by the detector 54 to the processor 56. At the processor 56, a determination is made whether the sensed parameter is greater than a threshold 82. If not, then monitoring continues. If the threshold is exceeded, then monitoring can still continue, but in step 84, the processor initiates a control sequence to operate the analytical sample capture device 38.

The processor 56 sends a control signal to the control port 60 on the inlet valve to open the valve. The processor also sends a control signal to the control port 70 on the air pump 68 to control the air pump. Thus, the processor 56 causes the air pump 68 to operate and draw air through the analytical sample capture device 38. In accordance with an aspect of the present invention, the processor 56 can control the speed of the air pump 68 to control the volume of air drawn in. In other aspects of the present invention, the air pump 68 operates at a constant volumetric capacity, and the processor 56 simply turns the air pump 68 on and off. While the air pump 68 is on, air is drawn through the sample collection device 66. The flow meter 62 measures the rate of the air flow. That information is provided on an output port 64 of the flow meter 62 to the processor 56.

In step 86, the processor issues an alert to an operator that a threshold was reached and that sample collection is under way. In step 88, the processor 56 determines whether sample collection by the device 38 should continue. In step 90, the processor 56 determines whether control is by an elapsed time and then determines whether a specified time has elapsed. The processor 56 can also alternatively determine whether a present flow volume has been achieved. The processor 56 can do so by monitoring the output of the flow meter. If it has, then in step 92, the processor 56 stops the collection of the sample. The processor 56 does this by sending a control signal to the control port 70 of the air pump 68 to instruct the air pump 68 to turn off. The processor 56 also sends a control signal to the control port 60 of the air inlet block valve 58 instructing the valve to close. The processor 56 also sends a signal to an operator indicating that a collection has occurred.

In step 94, the processor 56 determines whether an operator has intervened to end sampling. If not, sampling continues. If intervention occurred, then in step 92, the sample collection by the device 66 stops.

In accordance with another aspect of the present invention, the processor 56 can determine whether to stop the collection according to the type of removable apparatus in the analytical sampling control device. The processor 56 can be informed of the type of removable analytical sample collection device is being used, for example, by operator entry. Then the processor 56 determines when to stop based on the type of removable device. If the removable device is a sampling bag, the processor 56 stops sampling after a predetermined volume or time. The volume is determined by monitoring the output of the flow meter. If an evacuated canister is being used, the processor 56 stops collection after a predetermined or preset time has expired. If a cartridge or tube is used, then the processor 56 stops after a preset or predetermined time or volume has been reached.

In accordance with an aspect of the present invention, any sample collection device having a removable collector device can be used. For example, the removable collector device can be a tube containing a sampling medium or sorbent selected from the group consisting of: charcoal, Tenax, and silica gel. It can also be a cartridge with a filter or other sampling medium selected from the group consisting of PVC, MCEF, and PUF. It can also be an evacuated canister, e.g., Summa canister. It can also be a sample collection bag. The sample collection bag can be Tedlar or Mylar.

FIG. 4 illustrates the components of the analytical sampling control device ordered in a certain way in accordance with an aspect of the present invention. The components of the analytical sampling control device, in accordance with an aspect of the present invention, includes only an air inlet valve 58, a flow meter 62, an analytical sampling collection device 66 and an air pump, all mounted within a enclosure. The control ports 60 and 70 of the inlet block valve 58 and the air pump 68, respectively, and the output port 64 of the flow meter 62 have corresponding interfaces on the enclosure that allow the processor 56 to be connected to these ports. The inlet valve 58 precedes the sample collection device 66 in the order of components, however, the other components can be ordered in any way desired. In accordance with another aspect of the present invention, no pre-filter is included in the analytical sampling control device.

The results of a detector 54 in one field station can be used to control the sample collection device 66 in the same field station and/or in another field station. Thus, if an event that warrants further sampling is detected by one detector 54 in a first field station, the processor 56 in that first field station can initiate a collection by the sample collection device 66 in the first field station in the manner described above. The processor 56 can also initiate a collection by a sample collection device 66 in another field station in any way desired. To do so, the processor 56 sends a control signal to a base station 10 with instructions that another field station should initiate a sample collection by its sample collection device 66. The processor 56 or the base station 10 can specify a time for the second (or third or fourth etc.) collection. Thus, for example, if it is known that the wind is blowing in a certain direction, the base station 10 can instruct other field stations located downwind to collect samples with a sample collection device 66 located in the downwind field station. The base station can instruct those collections to occur at a certain time based on a speed and direction of a wind which is determined by any detector 54. In addition, sampling can be invoked by a combination of two or more of the above input parameters.

In accordance with an aspect of the present invention, the environmental detectors can perform a particulate sample test, e.g., measuring total particulates, PM–10. PM2.5, etc or some combination thereof. Further, the sample capture device can capture one of the following: asbestos, lead, hexavalent chromium, diesel exhaust, and products of combustion, such as soot. In another embodiment of the present invention, any of the environmental detectors can perform a total volatile organic compound test. In a further embodiment of the present invention, the sample capture device can capture an organic compound or group of compounds.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims.

I claim:

1. An environmental field station system to collect an environmental sample for a laboratory to determine a concentration of a first material in the environmental sample, comprising:
   a first environmental field station, comprising:
      an enclosure with an air intake;
      one or more environmental sensors mounted in the enclosure, each of the environmental sensors detecting an environmental condition;
      an analytical sampling collection device mounted in the enclosure, the analytical sampling collection device having a controllable inlet block valve, a flow meter with an output, a removable analytical sample capture device that is designed to be removed from the analytical sampling collection device and a controllable air pump;
      a processor mounted in the enclosure, the processor being connected to the one or more environmental sensors to receive environmental conditions sensed by the one or more environmental sensors; the processor also being connected to the controllable inlet block valve and the controllable air pump in the analytical sample capture device;
      wherein the processor is configured to open the controllable inlet block valve and/or to turn on the controllable air pump in the sample collection device to collect the environmental sample in the removable analytical sample capture device for the laboratory to determine a concentration of the first material when one of the one or more environmental sensors detects an environmental condition warranting initiation of sample collection and to stop collecting the environmental sample in the removable analytical sample capture device after an ending condition, based on a characteristic of the removable analytical sample capture device, has been met; and
      wherein the processor is configured to generate a message that the environmental sample has been obtained; and
   a processor in a base station to instruct, based on the environmental condition detected by the one or more environmental sensors, a second environmental field station located in a position determined by a target range of a wind direction to collect an environmental sample in a removable container.

2. The environmental field station of claim 1, wherein the one or more environmental sensors are selected from the group consisting of: dust sensors, gas sensors, vapor sensors, noise sensors, vibration sensors, radiation sensors and weather instruments.

3. The environmental field station of claim 1, wherein the analytical sample capture device is a tube containing a sampling medium or sorbent selected from the group consisting of: charcoal, Tenax, and silica gel.

4. The environmental field station of claim 1, wherein the analytical sample capture device is a cartridge with a filter or other sampling medium selected from the group consisting of PVC, MCEF, and PUF.

5. The environmental field station of claim 1, wherein the analytical sample capture device is an evacuated canister.

6. The environmental field station of claim 1, wherein the analytical sample capture device is a sample collection bag.

7. The environmental field station of claim 6, wherein the sample collection bag is Tedlar or Mylar.

8. The environmental field station of claim 1, wherein the processor is connected to the flow meter in the sample collection device and a flow rate is reported from the flow meter to the processor.

9. The environmental field station of claim 1, wherein the processor is preprogrammed to determine when the environmental condition warrants initiation of sample collection.

10. The environmental field station of claim 9, wherein the processor determines that the environmental condition warrants initiation of sample collection when the environmental condition exceeds a predetermined threshold.

11. An environmental monitoring system to collect an environmental sample for a laboratory to determine a concentration of a first material in the environmental sample, comprising:
   a base station;
   a plurality of environmental field stations, each comprising an enclosure with an air intake; one or more environmental sensors mounted in the enclosure, each of the environmental sensors detecting environmental conditions; an analytical sampling control device mounted in the enclosure, each of the analytical sampling control devices having a controllable inlet block valve, a flow meter with an output, a removable analytical sample capture device that is designed to be removed and a controllable air pump; and a processor mounted in the enclosure, the processor being connected to the one or more environmental sensors to receive environmental conditions sensed by the one or more environmental sensors; the processor also being connected to the controllable inlet block valve and the controllable air pump in the analytical sampling control device; wherein the processor opens the controllable inlet block valve and/or turns on the controllable air pump in the analytical sampling control device when one of the one or more environmental sensors detects an environmental condition, as previously specified by an operator or programmed or calculated in the processor, warranting initiation of sample collection to collect the environmental sample in the removable analytical sample capture device for the laboratory to determine the concentration of the first material and the processor stops collecting the environmental sample in the removable analytical sample capture device after an ending condition based on a characteristic of the removable analytical sample capture device has been met;
   wherein the processor in each of the environmental field stations communicates with the base station and the base station controls an analytical sampling control device in one of the plurality of environmental field stations based on a detected environmental condition in another of the plurality of environmental field stations.

12. The environmental monitoring system of claim 11, wherein the analytical sample capture device is a tube containing a sampling medium or sorbent selected from the group consisting of: charcoal, Tenax, and silica gel.

13. The environmental monitoring system of claim 11, wherein the analytical sample capture device is a cartridge with a filter or other sampling medium, selected from the group consisting of PVC, MCEF, and PUF.

14. The environmental monitoring system of claim 11, wherein the analytical sample capture device is an evacuated canister.

15. The environmental monitoring system of claim 11, wherein the analytical sample capture device is a sample collection bag comprising Tedlar or Mylar.

16. The environmental field station system of claim 11, wherein the environmental condition warranting initiation of sample collection is a target range of a wind direction for a first field station in the plurality of field stations which causes one or more field stations in the plurality of field stations to initiate a sample collection.

17. An environmental monitoring system to collect an environmental sample for a laboratory to determine a concentration of a first material in the environmental sample, comprising:
- a plurality of environmental field stations, each environmental field station comprising:
  - an enclosure with an air intake;
  - one or more environmental sensors to detect an environmental condition, including a wind direction;
  - a processor controlled removable analytical sample capture device to capture an environmental sample that is designed to be removed to the laboratory;
- a network to transmit data from and to the plurality of environmental field stations, including data of a wind direction measured by a first environmental field station in the plurality of environmental field stations to instruct the processor that controls the removable analytical sample capture device at a second environmental field station in the plurality of environmental field stations to capture the environmental sample.

* * * * *